United States Patent [19]

Triplett et al.

[11] 4,175,263

[45] Nov. 20, 1979

[54] TECHNIQUE FOR MONITORING WHETHER AN INDIVIDUAL IS MOVING FROM A PARTICULAR AREA

[75] Inventors: William C. Triplett, Ingleside; Richard B. A. Morrow, Corpus Christi, both of Tex.

[73] Assignee: Triad & Associates, Inc., Robstown, Tex.

[21] Appl. No.: 790,814

[22] Filed: Apr. 25, 1977

[51] Int. Cl.² .................................................. G08B 21/00
[52] U.S. Cl. ........................................ 340/573; 340/575; 340/666
[58] Field of Search ............... 340/279, 272, 573, 575, 340/666

[56] References Cited

U.S. PATENT DOCUMENTS

| 3,533,095 | 10/1970 | Collins | 340/279 |
| 3,777,175 | 12/1973 | Lewis et al. | 340/272 |
| 3,781,843 | 12/1973 | Harrison et al. | 340/279 |
| 4,020,482 | 4/1977 | Feldl | 340/279 |

*Primary Examiner*—Glen R. Swann, III
*Attorney, Agent, or Firm*—G. Turner Moller

[57] ABSTRACT

A first pressure sensor is positioned to sense the weight of part of the patient's body in the normal position and a second pressure sensor is positioned for sensing the weight of part of a patient's body when a patient begins to leave the bed. The device also includes an alarm and a pressure responsive switch connected to the first and second sensors to energize the alarm when the patient's weight is shifted from the first pressure sensor to the second pressure sensor. Another embodiment of the invention indicates when a patient moves from a recumbent to a sitting position or raises his head from a recumbent position. A further embodiment indicates when a child gets out of bed. Another embodiment of the invention indicates when a child moves out of an area where the child is supposed to be into an area where the child is not supposed to be.

19 Claims, 8 Drawing Figures

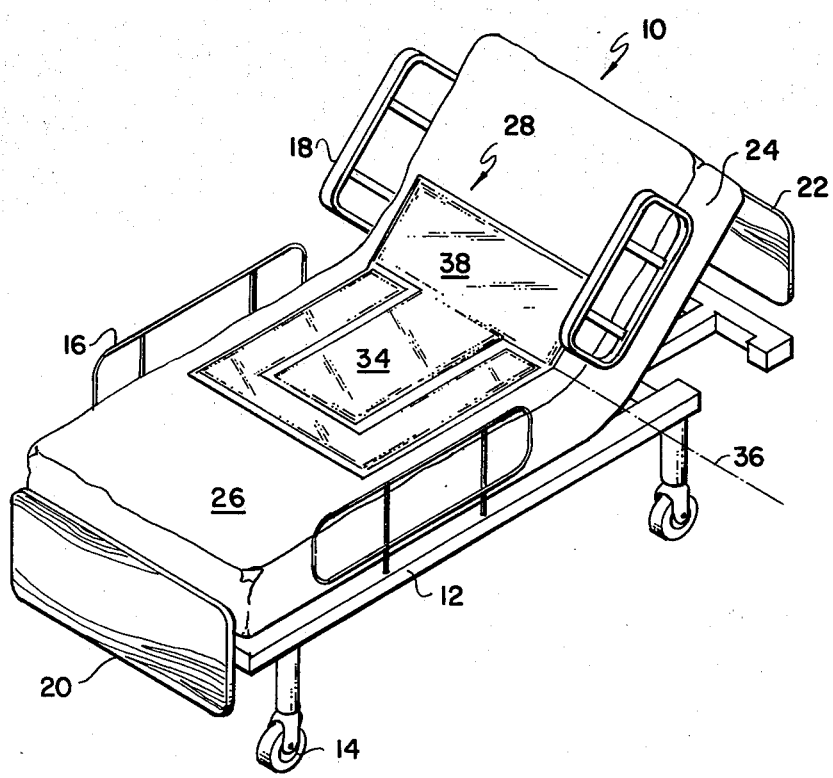
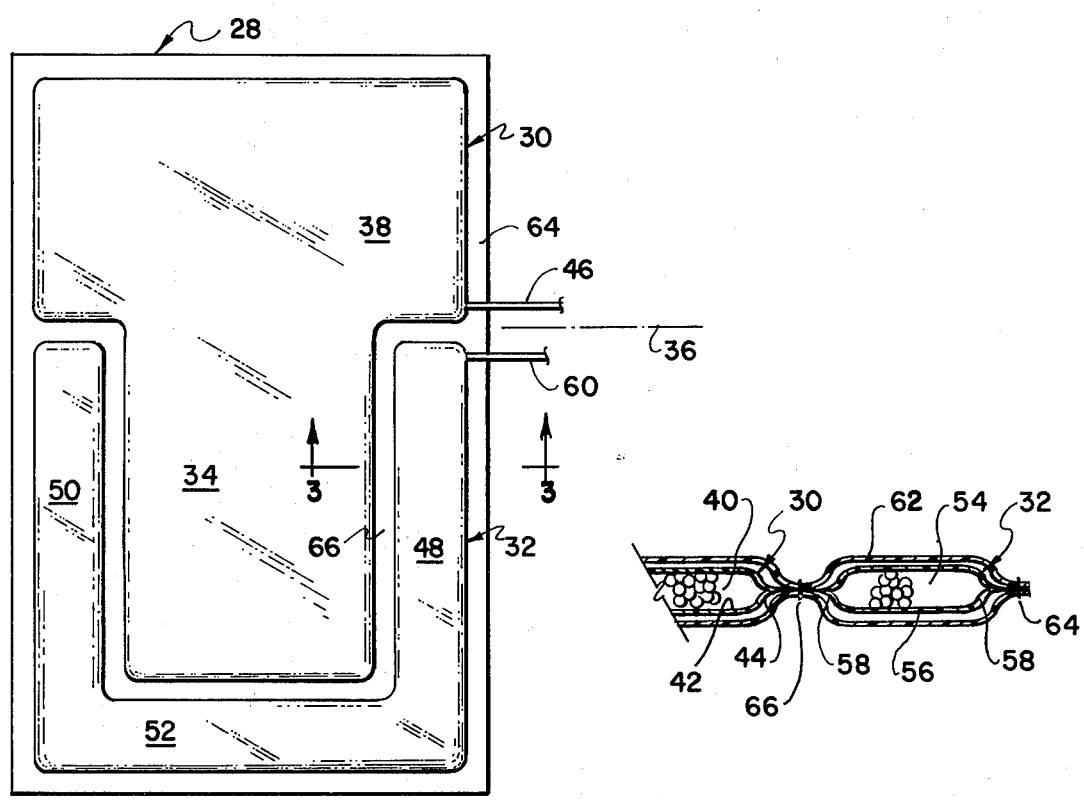
FIG. 1
FIG. 2
FIG. 3

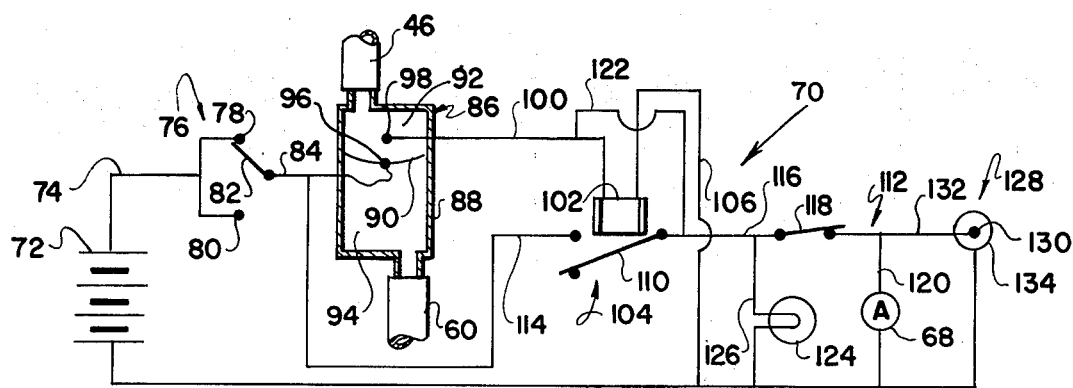
FIG. 4
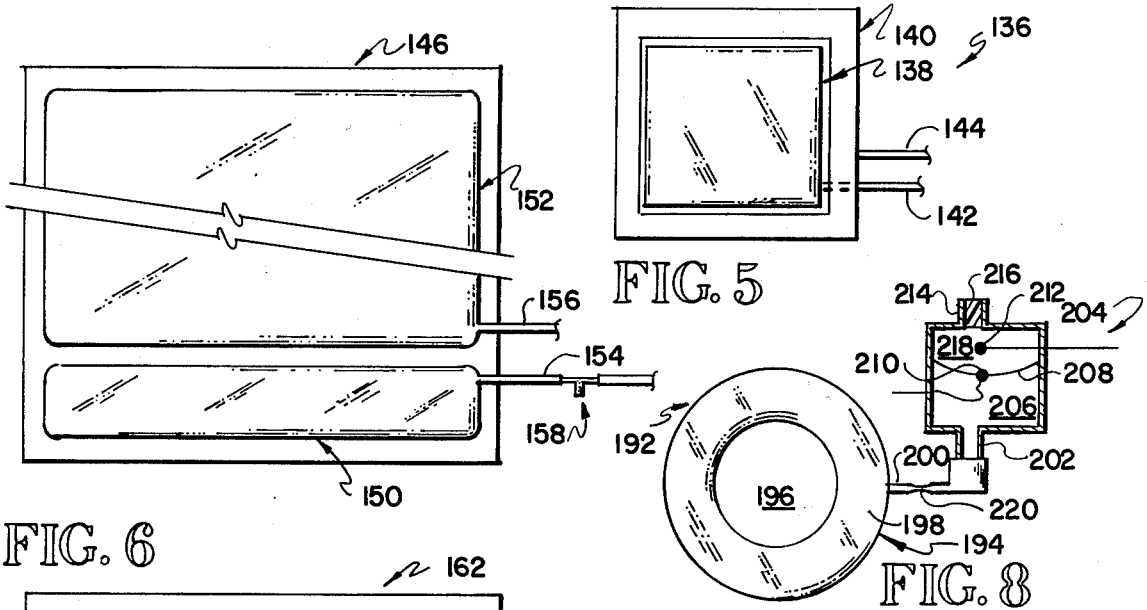
FIG. 5
FIG. 6
FIG. 8
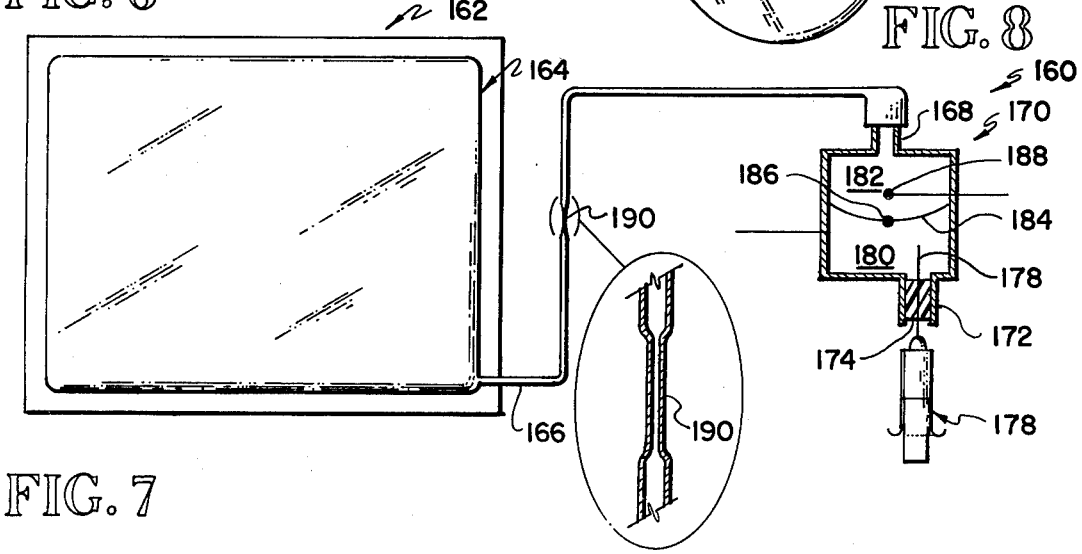
FIG. 7

TECHNIQUE FOR MONITORING WHETHER AN INDIVIDUAL IS MOVING FROM A PARTICULAR AREA

BACKGROUND OF THE INVENTION

This invention relates to a monitoring system for determining and indicating movement of an individual from one position to another. Several embodiments of the invention relate to determining and indicating when a patient is about to or is attempting to leave his bed. Another embodiment relates to determining and indicating when an individual merely raises his head from a recumbent position. Another embodiment relates to determining and indicates when a person, usually a child, is leaving a small area.

It is often desirable to know when an individual is attempting to crawl out of bed. This may occur, for example, in a hospital where the individual is an injured or ill adult or child; in a nursing home where the individual is an elderly or senile person; or in a nursery where the individual is a child. As used herein, the term patient is intended to encompass any individual who is supposed to remain in bed.

One of the common hospital accidents occurs when a patient climbs off of a hospital bed and is injured either by falling off the bed or by stumbling or falling after successfully getting out of bed. Because such accidents are, to a large extent, preventable, it is evident that there is a substantial interest in and need for a monitoring system to determine and indicate when a patient is in the process of getting out of bed without having to physically watch the patient at all times.

Essentially the same considerations are operative in nursing homes and other limited care facilities. In addition, there are numerous situations in a residence where it is desirable to know when an invalid, senile person or child is attempting to get out of bed.

It is accordingly not surprising that some effort has been expended in the development of devices to indicate when patients are getting out of bed or have gotten out of bed. For example, the disclosure in U.S. Pat. No. 3,852,736 utilizes a pressure or weight operative switch to sense the patient's weight. An alarm is energized when the switch is closed signifying an absence of patient weight. In this device, the weight sensitive switch is apparently basically a point sensor which indicates that the patient's weight is at a particular location which leads to false alarms when the patient merely rolls over in bed. False alarms have a particularly insidious effect because the attendant tends to disregard an alarm after the occurrence of one or more false alarms.

In U.S. Pat. No. 3,961,201, there is disclosed a pressure or weight sensitive switch located on the edge of a bed which trips an alarm upon the imposition of weight on the bed edge. Although this device is intended to detect when the patient is in the process of getting out of bed, the alarm can be falsely tripped merely by a visitor, for example, sitting on the edge of the bed. In U.S. Pat. No. 3,781,843, there is disclosed a device incorporating a pneumatic sensor in the guard rails of a hospital bed which trips an alarm when a weight is imposed on the guard rails. Although this device is likewise intended to indicate when a patient is in the process of climbing over the guard rails, false alarms are initiated merely by a visitor leaning on the guard rails.

It is also desirable, under certain circumstances, to know when a patient is moving from a recumbent position to a sitting position or when a patient is merely raising his head from a recumbent position, for example, when a patient has suffered a severe head injury and treatment dictates that the patient not raise his head.

It is also desirable, under certain circumstances, to know when an individual, typically a child, is moving out of a small area where the individual is known to be safe or where it is reasonable to expect that the individual will not over exert.

The present invention overcomes the foregoing and other disadvantages of the prior art by providing a novel and improved device for indicating when a patient is shifting weight on a bed from a normal recumbent or sitting position to another position indicative of egress from the bed.

SUMMARY OF THE INVENTION

One embodiment of the device of this invention includes a first pressure sensing pad of considerable areal extent positioned on a bed for sensing the weight of part of the patient's body in the normal position. The first pressure sensing pad preferably comprises an open pore foam material of relatively large areal extent placed on top of the mattress and either above or below suitable bed coverings. The open cell foam is encapsulated in an impermeable sheath or envelope through which extends a conduit for transmitting fluid to a remote pressure operated switch.

A second pressure sensor, which may be incorporated in a guard rail if desired, preferably comprises a pressure pad of considerable areal extent located on the horizontal part of the bed. The second pressure sensor is located to sense the weight of part of the patient's body in a position indicative of impending egress from the bed. The pad of the second pressure sensor is preferably made in substantially the same manner as the first pressure sensing pad.

Means are provided for energizing an alarm in response to the shifting of weight from the first pressure pad to the second pressure pad which is indicative of impending patient egress. The energizing mechanism is designed to operate upon the occurrence of two conditions: (1) the reduction of patient weight from the first pressure sensor and (2) the increase in weight on the second pressure sensor. In this fashion, false alarms are substantially minimized because the alarm is not tripped merely by increase of weight on the second pressure sensor, as may occur when a visitor sits or leans thereon.

It is an object of this invention to provide an improved patient monitoring system and particularly such a system which indicates impending patient egress from a bed with a minimal occurrence of false alarms.

Another object of the invention is to provide a patient monitoring system for determining and indicating when a patient raises his head from a bed.

Still another object of the invention is to provide a monitoring system for indicating when a person is moving out of a small predetermined area.

Other objects and a fuller understanding of the invention may be had by referring to the following description and claims taken in conjunction with the accompanying drawings.

IN THE DRAWINGS

FIG. 1 is an isometric view of a typical hospital bed having a pressure sensing mechanism thereon in accordance with the principles of this invention;

FIG. 2 is a plan view of the pressure sensing mechanism illustrated in FIG. 1;

FIG. 3 is an enlarged cross-sectional view of the pressure sensing mechanism of FIG. 2 taken substantially along line 3—3 thereof as viewed in the direction indicated by the arrows;

FIG. 4 is a largely schematic view of a control circuit utilized with the pressure pad of FIG. 2 to trip an alarm upon impending patient egress from the bed;

FIG. 5 is a plan view of another embodiment of the pressure sensing pad of this invention;

FIG. 6 is a plan view of another embodiment of the pressure sensing pad of this invention utilized in a somewhat different manner;

FIG. 7 is still another embodiment of the pressure sensing pad of this invention in combination with a slightly different control circuit.

FIG. 8 is a view of another embodiment of the pressure sensing pad of this invention utilized in a somewhat different manner.

DETAILED DESCRIPTION OF THE PREFERRED EMBODIMENTS

Referring to FIG. 1, there is illustrated a conventional hospital type bed 10 comprising a frame 12 having wheels or casters 14 thereon supporting an articulated frame (not shown) on which is supported a pair of main guard rails 16 and a pair of torso guard rails 18. A footboard 20 and headboard 22 are supported on the frame 12 in any suitable fashion. A mattress 24 lies on the articulated frame and moves in conformance therewith.

Positioned on the mattress 24 above a mattress pad 26 and preferably below bed coverings such as sheets and the like is a weight sensing mechanism 28 of this invention. As shown best in FIGS. 2 and 3, the weight sensing mechanism 28 is of generally rectangular configuration and provides a first pressure sensing pad 30 for sensing the weight of part of the patient's body in a normal recumbent or sitting position. The pressure sensing mechanism 28 also comprises a second pressure sensor located to sense the weight of part of the patient's body in a position indicative of patient egress from the bed 10. Although the second pressure sensor may be incorporated in the main guard rails 16 in a fashion illustrated in U.S. Pat. No. 3,781,843, it is preferred that the second pressure sensor comprise a pad 32 on the horizontal part of the bed 10.

The first pressure sensing pad 30 comprises a structure of generally T-shape in plan having a central portion 34 extending down the center of the mechanism 28 and down the center of the mattress 24 between an axis 36 defined by the bend in the articulated frame (not shown) of the bed 10 and the lower part of the mechanism. The central portion 34 is accordingly subjected to part of the weight of the patient in either a recumbent or sitting position. The pressure sensing pad 30 also comprises a section 38 extending across the width of the mechanism 28 adapted to sense the patient's weight in the recumbent position. It is thus apparent here that the weight sensing mechanism 28 is of considerable areal extend, e.g. in the range of 8-25 square feet and preferably on the order of 10-15 square feet. In a prototype of the invention, the mechanism 28 is on the order of 4' long and 3' wide.

As shown best in FIG. 3, the central portion 34 and section 38 comprise an open cell foam layer 40 which is filled with a fluid, preferably air, for actuating an external pressure responsive switch as will be more fully apparent hereinafter. The foam layer 40 may be of any suitable type and construction although a simple open cell latex foam pad operates quite satisfactorily. Encapsulating the foam layer 40 is an envelope 42 of a material impermeable to the fluid in the foam layer 40. A heavy duty polyvinyl chloride sheeting works quite successfully and is heat sealed or vulcanized along a peripheral seam 44 in a manner apparent to those skilled in the art. A conduit 46 extends into the envelope to allow fluid passage between the foam layer 40 and a pressure operated switch as will be more fully explained hereinafter.

The second pressure sensing pad 32 is generally U-shaped in plan bounding the edges of the central portion 34 and comprises a pair of legs 48, 50 parallel to the longitudinal dimension of the mattress 44 and a leg 52 perpendicular thereto. The legs 48, 50, 52 may be of the same type of construction as the portion 34 and section 38 but preferably comprises an open cell foam layer 54 encapsulated by an envelope 56 sealed in any suitable fashion along its peripheral margin 58. A conduit 60 extends into the envelope 56 and provides communication to a pressure actuated switch as more fully explained hereinafter.

As is apparent, the pressure pads 30, 32 are pressure independent although they may be mechanically interconnected as by enclosing both pads in a cover or envelope 62 of any suitable material stitched along an exterior margin 64 of the mechanism 28 and stitched along the boundary 66 between the pads 30, 32.

Referring to FIG. 4, there is illustrated an alarm 68 and circuit 70 for energizing the alarm 68 in response to the shift of patient movement from the first pad 30 to the second pad 32. The circuit 70 comprises a power source 72, preferably a battery, connected to a lead 74 communicating with the reset switch 76 comprising a first contact 78 and a second contact 80 along with a moveable switch element 82. The switch element 82 is connected to a lead 84 extending to a pressure differential switch 86.

The pressure differential switch 86 may be of any suitable type, for example a Fairchild PSF 100A or the like, comprising a housing 88 divided by a diaphragm 90 into first and second compartments 92, 94 respectively communicating through the conduits 46, 60 to the first and second pressure sensing pads 30, 32 respectively. The lead 84 is connected to a contact 96 carried by the diaphragm 90 for movement toward and away from a stationary contact 98 in communication with a lead 100 extending out of the housing 88. As will be more fully apparent hereinafter, the existence of pressure in the compartment 92 resulting from the weight of the patient on the first sensing pad 30 prevents movement of the diaphragm 90 and contact 96 into switch closing relation with the contact 98 even upon the increase of pressure in the compartment 94 caused by visitor sitting on the edge of the bed 10 and on the second pressure sensing pad 32. It is accordingly evident that false tripping of the alarm 68 is largely prevented.

The lead 100 connects to one terminal of a coil 102 of a relay 104 of any suitable type. A typical satisfactory relay has a high coil sensitivity or a low activating current requirement of 8-10 milliamperes of which Radio Shack relay numbers 275-003 and 275-004 are exemplary. The opposite terminal of the coil 102 is connected to a lead 106 secured to a wire 108 leading to the battery 72 to complete the relay circuit.

When the relay coil 102 is energized, it closes a switch element 110 and an alarm subcircuit 112 comprising a lead 114 connected to the lead 84 and a wire 116 having a deactivating or testing switch 118 therein secured to a lead 120 in series with the alarm 68 and the wire 108.

In order to maintain the relay switch 110 closed, a lead 122 connects the wire 116 and lead 100. After the switch 110 closes, the relay coil 102 is energized through the lead 122 so that the coil remains energized even though the switch contacts 96, 98 open, as when the patient moves completely off the weight sensing mechanism, i.e. gets completely out of the bed 10.

The alarm 68 may be of any suitable type and is preferably located in or immediately adjacent to the room in which the patient is staying. It is accordingly preferred that the alarm 68 be of the audible variety, for example an EICO Model SA15, although any suitable type of alarm may be employed.

A circuit testing feature is provided by an indicating lamp 124 in a lead 126 connected between the wires 108, 116 in conjunction with the testing switch 118. In order to determine if the pressure sensors 30, 32 and the energizing circuit 70 are operating satisfactorily, the testing switch 118 is open and the patient's weight is shifted from the first pressure pad 30 to the second pressure pad 32. If all components are operating satisfactorily, the lamp 124 will light thereby indicating that the system is functioning without sounding the alarm 68 and creating the resultant commotion.

In order to provide a remote alarm feature, the alarm subcircuit 112 may include a female jack receptacle 128 having a first terminal 130 connected to a lead 132 in circuit with the alarm 68 and a second terminal 134 connected to the wire 108. By inserting a two-wire jack into the receptacle 128, a signal inidicative of the patient getting out of bed may be transmitted to a remote location.

In use, the foam layers 40, 54 of the pressure sensors 30, 32 are slightly charged with a suitable fluid, for example air, and the conduits 46, 60 are connected to the pressure differential switch 86. So long as a substantial portion of the patient's weight remains on either or both the central portion 34 or the section 38 of the first pressure sensor 30, the compartment 92 is pressurized thereby preventing the diaphragm 90 from moving in a switch closing direction regardless of the weight applied to the second pressure sensing pad 72. As soon, however, as the patient begins leaving the first pressure sensing pad 30, pressure in the compartment 92 declines so that increased pressure in the compartment 94, caused by patient weight on the sensing pad 32, effects movement of the diaphragm 90 in a switch closing direction to engage the contacts 96, 98. When the contacts 96, 98 close, a circuit including the battery 72, the reset switch 76, the pressure differential switch 86 and the relay armature 102 is closed thereby closing the relay switch element 110. Closing of the switch element 110 completes the alarm subcircuit 112 to energize the alarm 68.

In order to turn off the alarm 68 and reset the energizing circuit 70, an attendant merely manipulates the reset switch 76 to move the switch element 82 into engagement with the contact 80. Because the reset switch 76 is of the break-before-make type, the coil 102 is temporarily deenergized, thereby allowing the switch element 110 to move to a switch open position under the bias of a spring (not shown) or gravity. If the patient is already back in bed, the pressure differential switch does not reactivate. On the other hand, if the attendant turns off the alarm 68 by manipulating the reset switch 76 before getting the patient back in bed, the alarm 68 will be reactivated when the patient gets back in bed because the pressure pad 32 will first be compressed thereby increasing the pressure in the compartment 94 which moves the diaphragm 90 in a switch closing direction. To avoid reactivating the alarm 68, the attendant may press on the pad 30 or open the testing switch 118. In the alternative, the attendant may allow the alarm 68 to go off and immediately deactivate the same by manipulating the reset switch 76.

Referring to FIG. 5, there is shown another embodiment 136 of a weight sensing mechanism which can be employed with the energizing circuit 70. The weight sensing mechanism 136 is of generally rectangular configuration and provides a first or central pressure sensing pad 138 for sensing part of the weight of the patient in either a normal recumbent position or a sitting position and a second peripheral pressure sensing pad 140 surrounding the first pad 138. The pressure sensing pads 138, 140 may be of substantially the same design as illustrated in FIG. 3 and comprise a pressure outlet conduit 142, 144 respectively connected to the compartments 92, 94 of the pressure differential switch 86 of FIG. 4. In use, the pad 138 is located between the knees and lower back of the patient. The weight sensing mechanism 136 has considerable application in beds not having a headboard or where the head of the bed is not placed against a wall which would allow a patient to climb over the head of the bed without compressing the pad 140.

Referring to FIG. 7, there is illustrated another embodiment 160 of the device of this invention comprising a weight sensing mechanism 162 including a pressure sensitive pad 164 of considerable areal extent and of similar construction to that illustrated in FIG. 3. Only a single conduit 166 exits from the pad 164 and connects to one inlet 168 of a pressure differential switch 170 which is substantially identical to the switch 86 except that the other inlet 172 is closed by a plug 174 of suitable material, for example rubber or plastic, which can be penetrated by a hollow needle 176 of a syringe 178.

In the device of FIG. 7, a predetermined switch closing pressure is imparted to the compartment 180 by air or other suitable gas injected therein from the syringe 178 which is subsequently removed. When the patient begins to leave the pad 164, the pressure in the compartment 182 declines thereby allowing the switch closing pressure to move the diaphragm 184 and close the switch contacts 186, 188 to energize a suitable alarm. The compartment 180 accordingly operates as a calibrated pressure source to close the switch contacts 186, 188 in the event the individual leaves the pad 164.

The embodiment 160 of this invention is believed particularly applicable to infants and children because they are normally more active than adults and cannot typically be relegated to the center of a bed. It will be apparent that the device 160 will not give a false alarm merely by the increase in pressure on the pad 164. In order to prevent closing of the switch 170 and the consequent sounding of an alarm merely by the child bouncing on the pad 164, a time delay mechanism may be employed in the form of an orifice 190 in the conduit 166 or a time delay circuit (not shown) in the circuit 70.

Referring to FIG. 6, there is shown another embodiment 146 of a weight sensing mechanism which can be employed with the energizing circuit 70 for slightly different purposes. The weight sensing mechanism 146 is designed to determine and indicate when a patient's head rises from a recumbent position. The weight sensing mechanism 146 is of generally rectangular configuration and provides a first pressure sensing pad 150 for sensing the weight of the patient's head in a normal recumbent position and a second pressure sensing pad 152 of much larger areal extent for sensing the weight of at least the patient's torso. The pressure sensing pads 150, 152 are preferably of substantially the same design as illustrated in FIG. 3 and comprise a pressure outlet conduit 154, 156 respectively connected to the compartments 92, 94 of the pressure differential switch 86 illustrated in FIG. 4. When the patient's head rises off of the pad 150, pressure in the compartment 92 declines allowing pressure in the compartment 94 to move the diaphragm 90 in a switch closing direction to energize the alarm 68. It will be appreciated that there is considerably more of the patient's weight applied to the pad 152 than to the pad 150. This would tend to increase pressure in the compartment 94 sufficiently to move the diaphragm 90 in a switch closing direction. This tendency may be overcome by the provision of a fitting 158 in the conduit 154 which allows the injection of a pressurized fluid, for example air, into the pad 150 and compartment 92 effectively to calibrate the switch 86.

Referring to FIG. 8, there is illustrated another embodiment 192 of this invention comprising a weight sensing mechanism 194 of annular configuration, which may be either circular, oval, polygonal or any other suitable configuration providing an open area 196 where a child or infant is supposed to remain surrounded by a pressure sensitive pad 198 of similar construction to that illustrated in FIG. 3. Only a single outlet 200 exits from the pad 198 and connects to one inlet 202 of a pressure differential switch 204 which is substantially identical to the switch 170 except that the inlet 202 is connected to a compartment 206 in which the pressure tends to move the diaphragm 208 in a direction to close the switch contacts 210, 212. The other inlet 214 is closed by a plug 216 of suitable material, for example rubber or plastic, which can be penetrated by a hollow needle of a syringe for charging the compartment 218 with air or other suitable fluid to a predetermined pressure.

When the individual begins to leave the area 196 and applies weight to the pressure sensing pad 198, pressure is transmitted through the conduit 202 to the compartment 206 to move the diaphragm 208 in a direction to close the contacts 210, 212 and sound the alarm.

The embodiment 192 of this invention is believed particularly applicable to infants or children where it is desired to determine and indicate that the child or infant is leaving the area 196. In order to prevent the closing of the switch 204 and the consequent sounding of the alarm merely by the child beating on the pad 198, a time delay mechanism may be employed, in the form of an orifice 220 in the conduit 200 or a time delay circuit (not shown) in the circuit 70.

One of the surprising features of the weight sensing mechanisms of this invention is that they operate satisfactorily when placed under a bed component, of more than nominal thickness. For example, the placement of a Grant's pulsating pad (which is used to minimize bed sores) between the weight sensing mechanism and the patient has not adversely affected operation of the device of this invention.

Although the invention has been described in its preferred forms with a certain degree of particularity, it is understood that the present disclosure of the preferred embodiments has been made only by way of example and numerous changes in the details of construction and the combination and arrangement of parts may be resorted to without departing from the spirit and scope of the invention as hereinafter claimed. It is intended that the patent shall cover, by suitable expression in the appended claims, whatever features of patentable novelty exist in the invention disclosed.

What is claimed is:

1. A monitoring system for determining and indicating when an individual is moving from a given location, comprising
   a pressure sensing pad for receiving part of the individual's weight, the pad including a layer of compressible permeable material for receiving a fluid therein, an envelope impermeable to the fluid and enclosing the material and a conduit extending through the envelope in communication with fluid in the material; and
   means for indicating when the individual is moving from the given location including
   an alarm, and
   means in circuit with the alarm for energizing the same including a pressure differential switch having a first pressure compartment, an inlet to the first compartment connected to the conduit, a second compartment, a first switch contact in one of the compartments, a second switch contact, and means separating the first and second compartments and movable in response to pressure differentials between the first and second compartments in switch contact opening and closing directions.

2. The monitoring system of claim 1 wherein the permeable layer is continuous, providing only one pressure sensor, and the pressure differential switch includes means for admitting and retaining a quantity of fluid in the second compartment, the pressure in the second compartment acting to bias the separating means in a switch closing direction.

3. The monitoring system of claim 1 wherein the internally compressible layer is of annular configuration providing a nonpressure sensitive interior area and the pressure differential switch includes means for admitting and retaining a quantity of fluid into the second compartment, the pressure in the second compartment acting to bias the separating means in a switch opening direction.

4. A device for indicating when a patient is shifting weight on a bed from a first normal recumbent position to a second position, comprising
   a first pressure sensor positionable on the bed for sensing the weight of part of the patient's body in the first normal recumbent position;
   a second pressure sensor positionable on the bed for sensing the weight of part of the patient's body in the second position;
   an alarm; and
   means for energizing the alarm in response to shifting of the patient's weight from the first sensor to the second sensor.

5. The device of claim 4 wherein the first and second pressure sensors comprise pads are mechanically interconnected and are pressure independent.

6. The device of claim 5 wherein the pads are of generally uniform thickness providing a width and length substantially greater than the thickness.

7. The device of claim 4 wherein the energizing means comprises means responsive to pressure in both of the pads.

8. The device of claim 7 wherein the energizing means comprises means responsive to a pressure reduction in the first sensor and a pressure increase in the second sensor.

9. The device of claim 8 wherein pressure responsive means comprises a pressure differential switch.

10. The device of claim 4 wherein the second pressure sensor is located in a position indicative of patient egress from the bed.

11. The device of claim 10 wherein the second sensor resides along at least one edge of the device and the first pad resides in the center of the device, the first and second sensors being juxtaposed.

12. The device of claim 10 wherein the combined configuration of the first and second pads is generally rectilinear.

13. The device of claim 10 wherein the first sensor comprises a first pad providing a first leg extending into the center of the device and a second leg extending generally transverse to the first leg along one edge of the device, the first pad generally describing a T in plan; and the second sensor comprises a second pad comprising a third leg parallel to the second leg along a diametrically opposed edge of the device from the second leg, a fourth leg extending along a third edge of the device and being generally parallel to the first leg and generally transverse to the third leg, and a fifth leg extending along a fourth edge of the device and being generally parallel to the first leg, the second pad generally describing a U in plan.

14. The device of claim 13 wherein the device comprises a long dimension positionable parallel to the long dimension of the bed, the first leg being parallel to the long dimension.

15. The device of claim 10 wherein the first sensor comprises a first pad in the center of the device, the second sensor comprises a second pad extending around at least three sides of the first pad.

16. The device of claim 15 wherein the second pad extends around all sides of the first pad.

17. The device of claim 4 wherein the second pressure sensor is located in a position indicative of the patient's head rising from the bed.

18. The device of claim 17 wherein the second pressure sensor comprises a pad extending along only one end of the device and positionable under the head of the patient.

19. The device of claim 18 wherein the first pressure sensor comprises a first pad of much larger areal extent than the second pad, the first pad being positionable under the torso of the patient.

* * * * *